US010820069B2

(12) United States Patent
Sieja et al.

(10) Patent No.: US 10,820,069 B2
(45) Date of Patent: Oct. 27, 2020

(54) COMPUTER-AIDED DISPATCH SYSTEMS AND METHODS UTILIZING BIOMETRICS TO ASSESS RESPONDER CONDITION AND SUITABILITY

(71) Applicant: Intergraph Corporation, Madison, AL (US)

(72) Inventors: Edward Michael Sieja, Madison, AL (US); Renz Angelo Santos, Huntsville, AL (US); Andrew James England, Athens, AL (US)

(73) Assignee: Intergraph Corporation, Madison, AL (US)

( * ) Notice: Subject to any disclaimer, the term of this patent is extended or adjusted under 35 U.S.C. 154(b) by 0 days.

(21) Appl. No.: 16/437,633

(22) Filed: Jun. 11, 2019

(65) Prior Publication Data

US 2019/0297399 A1 Sep. 26, 2019

Related U.S. Application Data

(63) Continuation of application No. 15/384,874, filed on Dec. 20, 2016, now Pat. No. 10,349,148.

(51) Int. Cl.
*G06Q 10/06* (2012.01)
*H04Q 9/00* (2006.01)
(Continued)

(52) U.S. Cl.
CPC ............. *H04Q 9/00* (2013.01); *A61B 5/0022* (2013.01); *G06Q 10/063114* (2013.01);
(Continued)

(58) Field of Classification Search
CPC ............................................ G06Q 10/063114
(Continued)

(56) References Cited

U.S. PATENT DOCUMENTS 6,106,459 A 8/2000 Clawson
6,198,394 B1 3/2001 Jacobsen et al.
(Continued)

FOREIGN PATENT DOCUMENTS

CN 102063665 B 5/2013
CN 104867340 A 8/2015
(Continued)

OTHER PUBLICATIONS

IEEE, "Monitoring of Arduino-based PPG and GSR Signals through an Android Device," IEEE Engineering in Medicine and Biology Society (EMBS) InternationalStudent Conference (ISC) 2016 Design Competition, 106 pages, 2016.
(Continued)

*Primary Examiner* — Sheree N Brown
(74) *Attorney, Agent, or Firm* — Nutter McClennen & Fish LLP

(57) ABSTRACT

A Computer-Aided Dispatch (CAD) system is specially configured to account for the physical condition of emergency personnel, which can affect their ability to effectively handle a particular incident. The CAD system tracks health, stress, and biometric status of each available emergency responder automatically and in real-time based on a wide range of collected information and to assess the suitability of available emergency responders to respond to a given emergency incident based upon such status information. Based on such status information, the CAD system can make intelligent recommendations to the emergency dispatcher by taking into account such things as the emergency responder's past experiences with a particular type of emergency incident, the current and cumulative status of the emergency responder, and projections as to the future condition of the emergency responder if dispatched to handle the emergency incident.

20 Claims, 13 Drawing Sheets

(51) Int. Cl.

| | |
|---|---|
| *G06Q 10/10* | (2012.01) |
| *G06Q 50/22* | (2018.01) |
| *G08B 21/04* | (2006.01) |
| *G08B 27/00* | (2006.01) |
| *A61B 5/00* | (2006.01) |
| *H04L 29/08* | (2006.01) |
| *H04B 1/034* | (2006.01) |
| *H04W 4/80* | (2018.01) |
| *H04W 4/90* | (2018.01) |

(52) U.S. Cl.
CPC ....... *G06Q 10/103* (2013.01); *G06Q 10/1091* (2013.01); *G06Q 50/22* (2013.01); *G08B 21/0453* (2013.01); *G08B 27/001* (2013.01); *H04B 1/0343* (2013.01); *H04L 67/02* (2013.01); *H04Q 2209/40* (2013.01); *H04Q 2209/70* (2013.01); *H04Q 2209/826* (2013.01); *H04Q 2209/84* (2013.01); *H04W 4/80* (2018.02); *H04W 4/90* (2018.02)

(58) Field of Classification Search
USPC .......................................................... 707/722
See application file for complete search history.

(56) References Cited

U.S. PATENT DOCUMENTS

| | | | |
|---|---|---|---|
| 6,952,164 B2 | 10/2005 | Junqua | |
| 7,091,852 B2 | 8/2006 | Mason et al. | |
| 7,245,216 B2 | 7/2007 | Burkley et al. | |
| 7,976,480 B2 | 7/2011 | Grajales et al. | |
| 8,396,191 B2 | 3/2013 | Clawson | |
| 8,428,961 B2 | 4/2013 | Greischar et al. | |
| 8,478,418 B2 | 7/2013 | Fahey | |
| 8,873,719 B2 | 10/2014 | Clawson | |
| 9,642,131 B2 * | 5/2017 | Bohlander | H04W 4/025 |
| 10,043,085 B2 | 8/2018 | Dejewski | |
| 10,321,039 B2 * | 6/2019 | Bohlander | H04N 5/23206 |
| 10,349,148 B2 | 7/2019 | Sieja et al. | |
| 10,520,378 B1 * | 12/2019 | Brown | A61B 5/6804 |
| 2003/0055934 A1 | 3/2003 | Lincke | |
| 2003/0069680 A1 | 4/2003 | Cohen et al. | |
| 2008/0267360 A1 | 10/2008 | Spector | |
| 2008/0278311 A1 | 11/2008 | Grange et al. | |
| 2009/0168975 A1 | 7/2009 | Clawson | |
| 2010/0214118 A1 | 8/2010 | Losee et al. | |
| 2012/0218102 A1 | 8/2012 | Bivens et al. | |
| 2012/0286933 A1 | 11/2012 | Hsiao | |
| 2013/0065628 A1 * | 3/2013 | Pfeffer | G08B 25/016 |
| | | | 455/521 |
| 2013/0073302 A1 | 3/2013 | Ryan et al. | |
| 2014/0167955 A1 | 6/2014 | Mahajan | |
| 2014/0364751 A1 | 12/2014 | Dugan | |
| 2015/0264550 A1 | 9/2015 | Johnson et al. | |
| 2015/0278732 A1 | 10/2015 | Fielder et al. | |
| 2016/0100302 A1 | 4/2016 | Barash et al. | |
| 2016/0192166 A1 | 6/2016 | deCharms | |
| 2017/0124505 A1 * | 5/2017 | Nakfour | G01C 21/3415 |
| 2017/0265045 A1 * | 9/2017 | Igumnov | H04W 4/90 |
| 2018/0114081 A1 * | 4/2018 | Dejewski | G06K 9/00892 |

FOREIGN PATENT DOCUMENTS

| | | |
|---|---|---|
| JP | 2001325689 A | 11/2001 |
| JP | 2004252854 A | 9/2004 |
| JP | 2014219854 A | 11/2014 |

OTHER PUBLICATIONS

International Searching Authority, International Search Report—International Application No. PCT/US2017/067009, dated Feb. 23, 2018, together with the Written Opinion of the International Searching Authority, 15 pages.

Korbinian Frank, Authorized officer European Patent Office, International Search Report—International Application No. PCT/US2017/047976, dated Nov. 17, 2017, together with the Written Opinion of the International Searching Authority, 15 pages.

Kurniawan et al., "Stress Detection from Speech and Galvanic Skin Response Signals," IEEE 26.sup.th International Symposium on Computer-Based Medical Systems (CBMS), 6 pages, Jun. 20-22, 2013.

Popkin et al., "A Preliminary Examination of Railroad Dispatcher Workload, Stress, and Fatigue," U.S. Department of Transportation, Federal Railroad Administration, Office of Research and Development, Washington, DC, Foster-Miller, Inc.—FinalReport, 146 pages, May 2001.

Villarejo et al., "A Stress Sensor Based on Galvanic Skin Response (GSR) Controlled by ZigBee," MDPI Open Access, Sensors, vol. 12, No. 5, pp. 6075-6101, May 10, 2012.

European Examination Report for European Patent Application No. EP 17 829 438.5 dated Mar. 24, 2020. 7 pages.

* cited by examiner

INCIDENT TYPE RECORD

Incident Type (e.g., missing person, robbery, burglary, etc.)

Required Personnel Qualifications (e.g., water rescue, hostage negotiation, etc.)

Required Equipment

Incident Stress Level (e.g., low-medium-high or scale)

*FIG. 2*

INCIDENT RECORD

Incident Identifier (e.g., for tracking purposes)

Incident Type (e.g., missing person, robbery, burglary, etc.)

Incident Location

Incident Status (e.g., open, dispatched, closed)

Personnel Dispatched

Equipment Dispatched

*FIG. 3*

RESPONDER RECORD

Responder Information

Responder Name

Responder Type (e.g., EMT, police, fire, SWAT, etc.)

Responder Qualifications (e.g., water rescue, hostage negotiation, etc.)

Baseline Status Information

Baseline Biometric Information (e.g., heart rate, skin temperature, GSR, etc.)

Baseline Stress Level (e.g., low-medium-high or scale)

Current Status Information

Current Biometric Information (e.g., heart rate, skin temperature, GSR, etc.)

Current Stress Level (e.g., low-medium-high or scale)

Current Disposition (e.g., occupied/unoccupied, available/unavailable)

Current Location (e.g., based on GPS information)

Other Information (e.g., enviromental information)

Per-Incident Status Information

Incident Biometric/Stress/Performance Information

Cumulative Status Information

Cumulative Biometric/Stress/Performance Information

Past Status Information

Past Biometric/Stress/Performance Information

Incident ID: 1234

Incident Description: Domestic Assault

Incident Stress Level: 6/10

Available Units

| Rank | Unit | Status | Type | Comments |
|---|---|---|---|---|
| 1 | LPD0005 | Available | Foot | Officer has special domestic assault training |
| 2 | LPD0004 | Available | Patrol | Current officer stress level is 9 |
| 3 | LPD0006 | Arrived | Bike | Closest unit but currently busy |

Incident Type A

| Category | Normalized Score | Weight (%) | Final Score |
|---|---|---|---|
| Time to Arrival | 8 | 80 | 6.4 |
| Stress Level | 5 | 10 | 0.5 |
| Qualification Match | 3 | 10 | 0.3 |
| | | | 7.2 |

*FIG. 13*

Incident Type B

| Category | Normalized Score | Weight (%) | Final Score |
|---|---|---|---|
| Time to Arrival | 8 | 40 | 3.2 |
| Stress Level | 5 | 40 | 2.0 |
| Qualification Match | 3 | 20 | 0.6 |
| | | | 5.8 |

*FIG. 14*

COMPUTER-AIDED DISPATCH SYSTEMS AND METHODS UTILIZING BIOMETRICS TO ASSESS RESPONDER CONDITION AND SUITABILITY

CROSS-REFERENCE TO RELATED APPLICATION(S)

This patent application is a continuation of, and therefore claims priority from, U.S. patent application Ser. No. 15/384,874 entitled Computer-Aided Dispatch Systems and Methods Utilizing Biometrics to Assess Responder Condition and Suitability filed Dec. 20, 2016, which is hereby incorporated herein by reference in its entirety.

TECHNICAL FIELD

The present invention relates to computer-aided dispatch systems, and more particularly to computer-aided dispatch systems that automatically assess the suitability of potential emergency responders to respond to a given incident based on health and biometric data.

BACKGROUND ART

In emergency situations, time is of the essence in dispatching emergency responders. Not only must an emergency responder be able to arrive at an incident quickly, but the right type of emergency responder must be dispatched to deal with the special circumstances of the incident. For example, a hostage situation might require an emergency responder with hostage negotiation skills, while a potential drowning situation might require an emergency responder with water rescue skills.

Computer-aided dispatch (CAD) systems are well known in the art, especially in the dispatching of emergency responders to various emergency incidents. Among other things, CAD systems typically gather and store information about available emergency responders including available emergency personnel (e.g., EMTs, firefighters, police officers, etc.) as well as available emergency vehicles (e.g., ambulances, fire vehicles, police vehicles, med-flight helicopters, boats, etc.) and related equipment (e.g., whether or not a particular vehicle is equipped with a "jaws of life"). For convenience, the term "unit" may be used herein to refer to one or more emergency responders and related equipment dispatched to an incident (e.g., a police unit may include a specific police vehicle and one or more police officers who are utilizing that police vehicle).

CAD systems typically also gather and store information about each emergency incident, such as, for example, the location and type of emergency, among others. Such information may be gathered and stored automatically (e.g., through any of a variety of computer-based communication systems) and/or by a call-taker who gathers the information and enters it into the CAD system. The CAD system then can assist dispatchers in assigning tasks for the emergency responders, for example, by making a recommendation of which emergency personnel and/or vehicle(s) to assign to a particular emergency incident based upon criteria such as the type of emergency, the proximity of emergency responders to the emergency location, the status of each available emergency responder (e.g., whether or not a particular emergency responder is currently responding to an emergency incident), necessary equipment for the emergency incident (e.g., jaws of life), necessary skills for the emergency incident (e.g. suicide negotiation skills, water rescue skills, etc.), or minimal turns (for long ladder fire trucks), among others.

After responding to an emergency incident, it is often required for a party to be transported to a facility, such as, for example, a hospital or detention center. Therefore, in addition to keeping track of emergency personnel and vehicles, some CAD systems also gather and store information about each of a number of available facilities, such as, for example, the type of facility, the location of the facility, and the services provided by the facility (e.g., general emergency care vs. specialty treatments), among others. The CAD system then can assist dispatchers in assigning an emergency responder to an emergency incident and then to a facility, for example, by making a facility recommendation based on criteria such as the type and severity of care needed by the patient or victim, the capabilities of available facilities, and the proximity of available facilities to the emergency location, among others. For example, a dispatcher typically would prefer to assign an ambulance to the closest hospital, but in some cases the CAD system may recommend a second hospital that is further away (e.g., the closest hospital may only provide general emergency care while the patient within the ambulance may require specialty treatment, such as cardiac care, that is only provided by the second hospital that is further away).

In the past, first responders often were required to check in with the emergency dispatcher on a regular basis via radio to essentially say "I am ok." In some cases, first responders additionally had the ability to issue a "unit emergency alarm" if equipped with device such as a digital radio, a mobile laptop device in the vehicle (e.g., Intergraph Mobile for Public Safety), or a mobile smartphone application (e.g., Intergraph Mobile Responder). If the first responder did not check in on time, the emergency dispatcher would reach out to the first responder for a status update—typically via radio. This cycle repeated throughout the duration of a first responder's shift. The contacts and the responses typically were saved in the CAD system for auditability.

Since this method was procedural and had no automation support behind it, there was always a communication lag between updates, which could lead to safety issues for the first responders and additional work for the emergency dispatchers. For example, if the first responder was incapacitated, then the first responder would be unable to check in or issue an alarm, which would place a burden on the emergency dispatcher to check in with the first responder and would cause delay in dispatching additional resources to attend to the emergency and/or to help the first responder. Also, in many cases, the first responder would issue the alarm by mistake (e.g., inadvertently hitting the send button in the heat of action), in which case the dispatcher would have to respond to the erroneous alarm, e.g., by dispatching unneeded resources or to confirm whether or not there was a legitimate emergency. This method also was unreliable and subjective in that it depended on the first responder to accurately report his or her status. For example, a first responder may be injured, tired, or placed under a great deal of stress and yet report to the emergency dispatcher that all is fine.

Later, devices were developed to generate a "unit emergency alarm" automatically, e.g., upon detecting the sound of a gunshot (e.g., using a built-in microphone) or upon detecting that the first responder has fallen or has not moved in some amount of time (e.g., using a built-in inertial sensor). Such devices could alert the emergency dispatcher even if the first responder was incapacitated, but also could be prone to generating erroneous alarms. Some devices additionally could provide location information to the emergency dispatcher, e.g., using GPS location.

Overall, methods and devices of the types discussed above provide minimal information to the emergency dispatcher regarding the status of the first responder. Furthermore, such methods and devices generally do not account for the physical condition of the emergency responders, which can affect their ability to effectively handle a particular incident. For example, an emergency responder who is still stressed following a shootout or is exhausted following a foot chase might be a bad choice to respond to a new incident even if that emergency responder can get to the incident sooner than other emergency responders and is otherwise qualified to handle the incident.

SUMMARY OF THE EMBODIMENTS

Embodiments include a computer-aided dispatch (CAD) system and a computer-aided dispatch (CAD) method configured to receive, for each of a plurality of responders, biometric sensor data generated by a biometric sensor device worn by the responder; store, in the CAD database, the received biometric sensor data and, for each of the plurality of responders, healthy range data derived from the biometric sensor data; receive information for an incident including an incident type and an incident location; determine a set of requirements for the incident based on the incident type; determine, for each of the plurality of responders, a current condition of the responder based on (a) the biometric sensor data generated by the biometric sensor device worn by the responder, (b) the healthy range data for the responder, and (c) elapsed time between discrete activities of the responder; evaluate relative suitability of the responders for the incident based on the current conditions of the responders relative to the set of requirements for the incident and the incident location; and produce a dispatch recommendation for the incident based on the relative suitability of the responders.

In various alternative embodiments, the biometric sensor data may include at least one of heart rate, skin temperature, or galvanic skin response. Determining a current condition of the responder may involve determining a stress level of the responder, e.g., by determining a normal stress level for the responder, determining a current stress level for the responder, and producing a numeric value quantifying the current stress level relative to the normal stress level. Producing a dispatch recommendation based on the relative suitability of the responders may involve determining if a given responder is under duress based on the determined current condition of the responder and dispatching assistance for the responder upon determining that the responder is under duress. Producing a dispatch recommendation also may involve determining a level of performance required for the incident, determining whether the given responder can meet the level of performance required for the incident based on the determined current condition of the responder, and determining whether to recommend the responder for the incident based on whether the responder can meet the level of performance required for the incident. Evaluating relative suitability of the responders for the incident may involve determining, for each of the plurality of responders, a predicted time of arrival at the incident based on a current location of the responder and the incident location; and determining, for each of the plurality of responders, a predicted future condition of the responder for the predicted time of arrival. The elapsed time for a responder may be within a current shift of the responder, in which case determining the current condition may be further based on the types and outcomes of the discrete activities of the responder within the current shift of the responder.

In various further embodiments, producing a dispatch recommendation for the incident may involve producing a graphical display for a dispatcher, the graphical display depicting the current condition relative to a range of condition levels. The graphical display may depict a gauge showing the current condition relative to the range of condition levels. The graphical display may depict an indicator that is color-coded to show the current condition relative to the range of condition levels.

In any of the above-described embodiments, for each of the plurality of responders, the biometric sensor device worn by the responder may be in communication with a smartphone running a CAD application that conveys the biometric sensor data to the CAD server subsystem.

BRIEF DESCRIPTION OF THE DRAWINGS

The foregoing features of embodiments will be more readily understood by reference to the following detailed description, taken with reference to the accompanying drawings, in which:

FIG. 2 schematically shows the types of information that may be maintained for each possible incident type (referred to here as an "Incident Type Record"), in accordance with various exemplary embodiments.

FIG. 3 schematically shows the types of information that may be maintained for each incident (referred to here as an "Incident Record"), in accordance with various exemplary embodiments.

FIG. 4 schematically shows the types of information that may be maintained for each responder (referred to here as a "Responder Record"), in accordance with various exemplary embodiments.

FIG. 10 is a schematic graphical user interface (GUI) screen of the type that may be displayed on the CAD dispatch client workstation, in accordance with certain exemplary embodiments.

FIG. 12 is a schematic graphical user interface (GUI) screen showing the types of information that may be provided to the dispatcher to assist with making a dispatch decision, in accordance with certain exemplary embodiments.

FIG. 13 provides one example of weighting for three categories, in accordance with one exemplary embodiment.

FIG. 14 provides another example of weighting for three categories, in accordance with another exemplary embodiment.

DETAILED DESCRIPTION OF SPECIFIC EMBODIMENTS

Definitions

Figure 1:
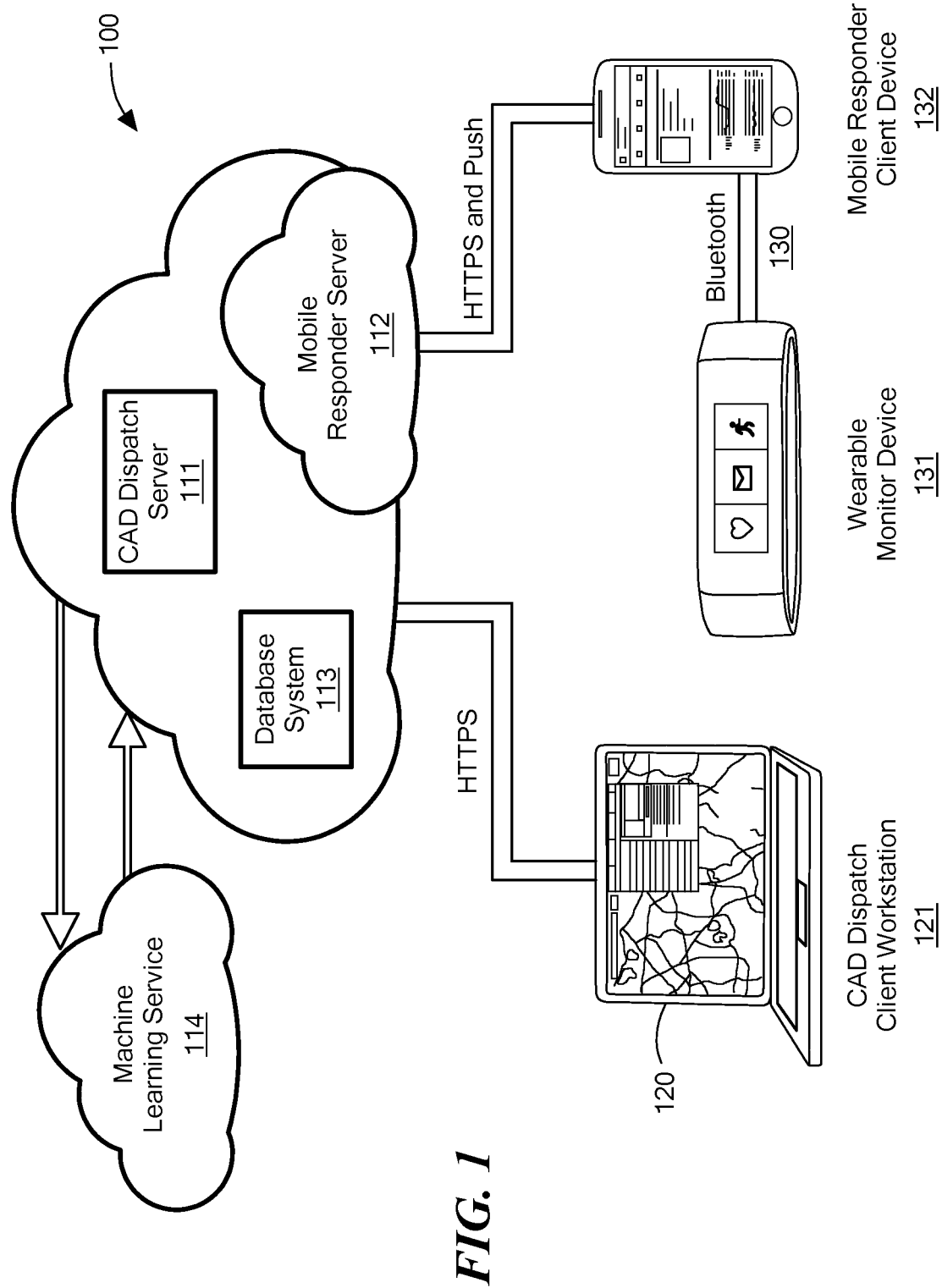
FIG. 1 is a simplified schematic diagram of a computer-aided dispatch (CAD) system, in accordance with certain exemplary embodiments.

As used in this description and the accompanying claims, the following terms shall have the meanings indicated, unless the context otherwise requires:

The term "unit" may be used herein to refer to one or more emergency responders and optionally also related equipment dispatched to an incident. For example, in some cases, a unit may refer to a specific vehicle (e.g., police car, fire engine, ambulance, etc.) and the personnel and/or equipment associated with that vehicle (e.g., police officer, fire fighter EMT, canine officer, etc.), while in other cases, a unit may refer to an individual person. In some cases, the terms "unit" and "emergency responder" may be used interchangeably.

A responder is deemed to be "under duress" if the responder is determined to have either an elevated stress level or a decreased capacity with respect to the responder's ability to handle a particular event. For example, a responder may be deemed to be "under duress" if the responder is partially or completely incapacitated (e.g., injured, unconscious, or dead) or otherwise requires assistance in handling a particular event.

A "set" includes one or more members.

As discussed above, not only must an emergency responder be able to arrive at an incident quickly, but the right type of emergency responder must be dispatched to deal with the special circumstances of the incident. Computer-aided dispatch (CAD) systems can assist dispatchers in assigning tasks for emergency responders, for example, by making a recommendation of which emergency personnel and/or vehicle(s) to assign to a particular emergency incident.

In embodiments of the present invention, the CAD system is specially configured to account for the physical condition and capabilities of emergency personnel, which can affect their ability to effectively handle a particular incident. Specifically the CAD system is configured to track health, stress, and biometric status of each available emergency responder automatically and in real-time based on a wide range of collected information and to assess the suitability of available emergency responders to respond to a given emergency incident based upon such status information. Specifically, the CAD system collects and tracks status information for each available emergency responder, including qualification status information (e.g., abilities and limitations of the responder), current status information (e.g., to assess the current condition of the emergency responder, such as tiredness, stress level, heart rate, temperature, etc.), prior status information (e.g., how has the emergency responder fared in the past when responding to this type of emergency incident or similar emergency incidents, how quickly does the emergency responder recover from stressful situations, etc.), and cumulative status information for the emergency responder's current shift (e.g., what types of incidents has the emergency responder been involved with during the shift, what actions did the emergency responder take during those incidents such as chasing or shooting at a suspect, etc.). Based on such status information, the CAD system can make intelligent recommendations to the emergency dispatcher by taking into account such things as the emergency responder's general and relative suitability to handle a particular emergency incident (e.g., is the emergency responder qualified, and is there someone more qualified or better suited to responding to the particular emergency incident), past experiences with a particular type of emergency incident, the current and cumulative status of the emergency responder, and projections as to the future condition of the emergency responder if dispatched to handle the emergency incident (e.g., in some cases, an emergency responder might calm down in the time it take to get to the emergency incident, while in other cases, an emergency responder might show up to the emergency incident with increased stress). The CAD system also can identify when an emergency responder is under duress or otherwise requires assistance and can make intelligent recommendations to the dispatcher for providing such assistance.

FIG. 1 is a simplified schematic diagram of a computer-aided dispatch (CAD) system 100, in accordance with certain exemplary embodiments. Among other things, components of the CAD system 100 can be logically divided into a number of subsystems including a CAD server subsystem 110, a dispatcher subsystem 120, and a personnel subsystem 130. Embodiments of the exemplary CAD system 100 can (and typically do) have multiple instances of each subsystem. For example, an exemplary CAD system 100 can include one personnel subsystem 140 for each emergency responder, multiple dispatcher subsystems 130 to allow for multiple emergency dispatchers to handle emergency calls and alerts within a single dispatch center and/or across multiple dispatch centers, and multiple CAD server subsystems 110 at one or more data centers to provide for such things as high-availability service and load balancing.

The CAD server subsystem 110 includes a CAD dispatch server 111 that interfaces with one or more dispatcher subsystems 120 over a first communication network, a mobile responder server 112 that interfaces with one or more personnel subsystems 130 over a second communication network, a database system 113 in which various types of data are maintained by the CAD dispatch server 111 and/or the mobile responder service 112, and optionally a machine learning service 114 that performs machine learning of various dispatch-related parameters as described herein.

The dispatcher subsystem 120 includes a CAD dispatch client workstation 121 that the emergency dispatcher uses to manage dispatch-related information. For example, among other things, the dispatcher may use the CAD dispatch client workstation 121 to enter information regarding incidents and emergency responders, view the status of incidents and responders, dispatch emergency responders, and interact with emergency responders such as by providing updated incident information.

The personnel subsystem 130 includes a monitor device 131 that is wearable by the emergency responder (e.g., a bracelet-type device) and a mobile responder client device 132 (e.g., a smartphone-type device running a specially-configured mobile responder client application). The wearable monitor device 131 is in communication with (e.g., "paired" with) the mobile responder client device 132 over a wireless communication system (e.g., Bluetooth or WiFi). The mobile responder client device 132 is in communication with the CAD server subsystem 110 over the second communication network, which may include a wireless communication system such as cellular telephone/data network.

The mobile responder client device 132 is specially configured (e.g., using special hardware and/or a purpose-built client application) to transfer various types of information between the wearable monitor device 131 and the CAD server subsystem 110, although certain types of information can be exchanged between the mobile responder client device 132 and the CAD server subsystem 110 exclusive of the wearable monitor device 131. Among other things, as discussed in greater detail below, the mobile responder client device 132 may transfer information from the wearable monitor device 131 and/or the mobile responder client device 132 itself to the CAD server subsystem 110, e.g., to allow for monitoring the emergency responder, and also can receive information from the CAD server subsystem 110 for presentation to the emergency responder on the mobile responder client device 132 and/or the wearable monitor device 131 via transfer from the mobile responder client device 132. The mobile responder client device 132 may provide a special graphical user interface through which the emergency responder can send and/or receive various types of information.

In accordance with certain exemplary embodiments, the wearable monitor device 131 includes one or more interface devices to collect status information about the emergency responder (referred to herein for convenience as "biometric" information). For example, the wearable monitor device 131 may include one or more of a heart-rate sensor, a skin temperature sensor, a galvanic skin response sensor, a blood oxygen level sensor, and/or other sensor for collecting biometric information. The wearable monitor device 131 transmits information derived from the interface devices to the mobile responder client device 132, which may be configured to process the information and/or transmit the information to the CAD server subsystem 110 for processing.

The wearable monitor device 131 and/or the mobile responder client device 132 may include other types of interface devices, such as, for example, a microphone (e.g., to allow the emergency responder to speak to an emergency dispatcher or to monitor for gunshots or other sounds), a speaker (e.g., to allow an emergency dispatcher to speak to the emergency responder or to generate audible alerts to the emergency responder by the CAD server subsystem 110 or the emergency dispatcher), a camera (e.g., to allow the emergency responder to record pictures or videos for evidentiary purposes and/or to send to the CAD server subsystem 110 or emergency dispatcher), a tactile output device such as a vibrator device (e.g., to generate tactile alerts to the emergency responder by the CAD server subsystem 110 or the emergency dispatcher), a "unit emergency alarm" input (e.g., a button to allow the emergency responder to generate an alarm to the CAD server subsystem 110 or emergency dispatcher), a motion sensor such as an accelerometer or gyroscope (e.g., to monitor whether the emergency responder is moving or stationary), a position sensor (e.g., to monitor whether the emergency responder is upright or recumbent), a temperature sensor (e.g., to monitor the environmental temperature in which the emergency responder is operating), and/or a location sensor such as a GPS sensor (e.g., to provide location information to the emergency dispatcher), among others. Information derived from such interface devices may be processed by the mobile responder client device 132 and/or sent to the CAD server subsystem 110 for processing.

Thus, for example, the first responder may be monitored through information obtained exclusively from the wearable monitor device 131 or may be monitored through a combination of information obtained from the wearable monitor device 131 and information obtained from the mobile responder client device 132.

The mobile responder client device 131 may send information to the CAD server subsystem 110 at regular intervals (e.g., via a Web Service API) or upon request from either the responder or the dispatcher. Each paired wearable monitor device 132 and mobile responder client device 131 is uniquely identifiable to the CAD server subsystem 110 and security is preferably implemented to prevent data breaches, e.g., using HTTPS-based communications between the mobile responder client device 131 and the CAD server subsystem 110.

The CAD server subsystem 110 maintains various types of information in the database system 113. For example, among other things, the CAD server subsystem 110 maintains information on the various incident types that may occur, information on each incident that does occur, and information on each emergency responder.

FIG. 2 schematically shows the types of information that may be maintained for each possible incident type (referred to here as an "Incident Type Record"). Among other things, an Incident Type Record may include such things as an incident type (e.g., missing person, robbery, burglary, drug overdose, domestic violence, fire, etc.), required personnel qualifications for the incident type (e.g., water rescue skills, hostage negotiation skills, etc.), required equipment for the incident type (e.g., jaws of life, ladder, etc.), and implicitly or explicitly an incident stress level indication (e.g., low-medium-high or a scale such as 1-5 or 1-10). Thus, the database system 113 may include a plurality of Incident Type Records, with each Incident Type Record specifying operational information for a distinct incident type.

FIG. 3 schematically shows the types of information that may be maintained for each incident (referred to here as an "Incident Record"). Among other things, an Incident Record may include such things as an incident identifier (e.g., for tracking purposes), an incident type indicator (e.g., matching one of the incident types), incident location information (e.g., an address), incident status information (e.g., whether responders have been dispatched, whether the incident is ongoing or complete, the final disposition of the incident, etc.), and information regarding the personnel and equipment dispatched to the incident.

FIG. 4 schematically shows the types of information that may be maintained for each responder (referred to here as a "Responder Record"). Among other things, a Responder Record may include such things as responder information (e.g., responder name, responder type, responder qualifications, etc.), baseline status information, current status information, per-incident status information, cumulative status information, and past status information.

The responder qualification status information includes any of a variety of information relating to qualifications for responding to incidents, such as, for example, skills, limitations, physical condition, age, athletic ability, and medical restrictions, to name but a few. This qualification status information is generally collected separately from the biometric information, such as through a questionnaire, training history, medical examinations, or other sources.

The baseline status information is derived from the biometric information collected for the responder and provides a reference for determining the current stress level of the responder. The baseline status information might represent, for example, the typical biometric values or ranges of values when the responder is at rest.

The current status information may include such things as current biometric information (e.g., current readings from the wearable monitor device 131), a current stress level derived from the current biometric information relative to the baseline biometric information (e.g., based on galvanic skin response and/or other collected information), the responder's current disposition (e.g., whether or not the responder is available to respond to a new incident), current location of the responder (e.g., based on GPS information), and other information (e.g., environmental information that may be used in determining current stress level, such as environmental information).

The per-incident status information may include such things as biometric information, stress level information, and performance evaluation information for the responder relative to a particular incident to which the responder was dispatched. Thus, the per-incident status information may be derived from the current status information relative to the current activities of the responder. Per-incident status information associated with a given responder with respect to a given incident may be stored as part of the Incident Record maintained for that incident and additionally may be used to update the Incident Stress Level information in the Incident Type Record associated with the incident type based on experiential data from the responder and possibly also other responders with respect to the incident type. For example, the CAD server system 100 can assess the relative stress levels of multiple responders with respect to the incident type and set the Incident Stress Level in the Incident Type Record based on these relative stress levels, e.g., to the average stress level experienced by the responders. Thus, for example, if a typical responder experiences high levels of stress when responding to a particular type of incident, then the CAD server system 100 may set the Incident Stress Level in the Incident Type Record to indicate that this type of incident is considered a high stress incident.

The cumulative status information may include such things as biometric information, stress level information, and performance evaluation information for the responder encompassing all incidents to which the responder was dispatched during the responder's current (or most recent) shift. Thus, the cumulative status information may be derived from the per-incident status information for one or more incidents during the shift. For example, the cumulative status information may track the incidents to which the responder was dispatched, the order of those incidents, the outcomes of those incidents, the performance of the responder during each of those incidents, and other information. The cumulative status information can be used in making future dispatch decisions, particular for situations in which the cumulative aspects of a shift are relevant. For example, if a particular responder was just involved in a high-stress car chase, that responder may not be a good candidate to respond to a domestic violence situation because the stress of the car chase may hinder the responder's ability to effectively address the domestic violence situation.

The past status information may include such things as a history of past biometric information and past stress level information as well as past performance evaluation information, for example, in terms of how this responder reacts during various types of incidents. The past status information is essentially an archive of some or all of the other types of information collected and derived for the responder. The past status information for the responder and across all responders can be mined for a wide variety of analytical data such as, for example, trends by each responder and for each type of incident.

Generally speaking, the CAD server subsystem 110 receives biometric and other information from the mobile responder client device 132 (including information from the wearable monitor device 131) for each emergency responder on an ongoing basis and updates various records maintained in the database system 113 based on the received information.

Figure 5:
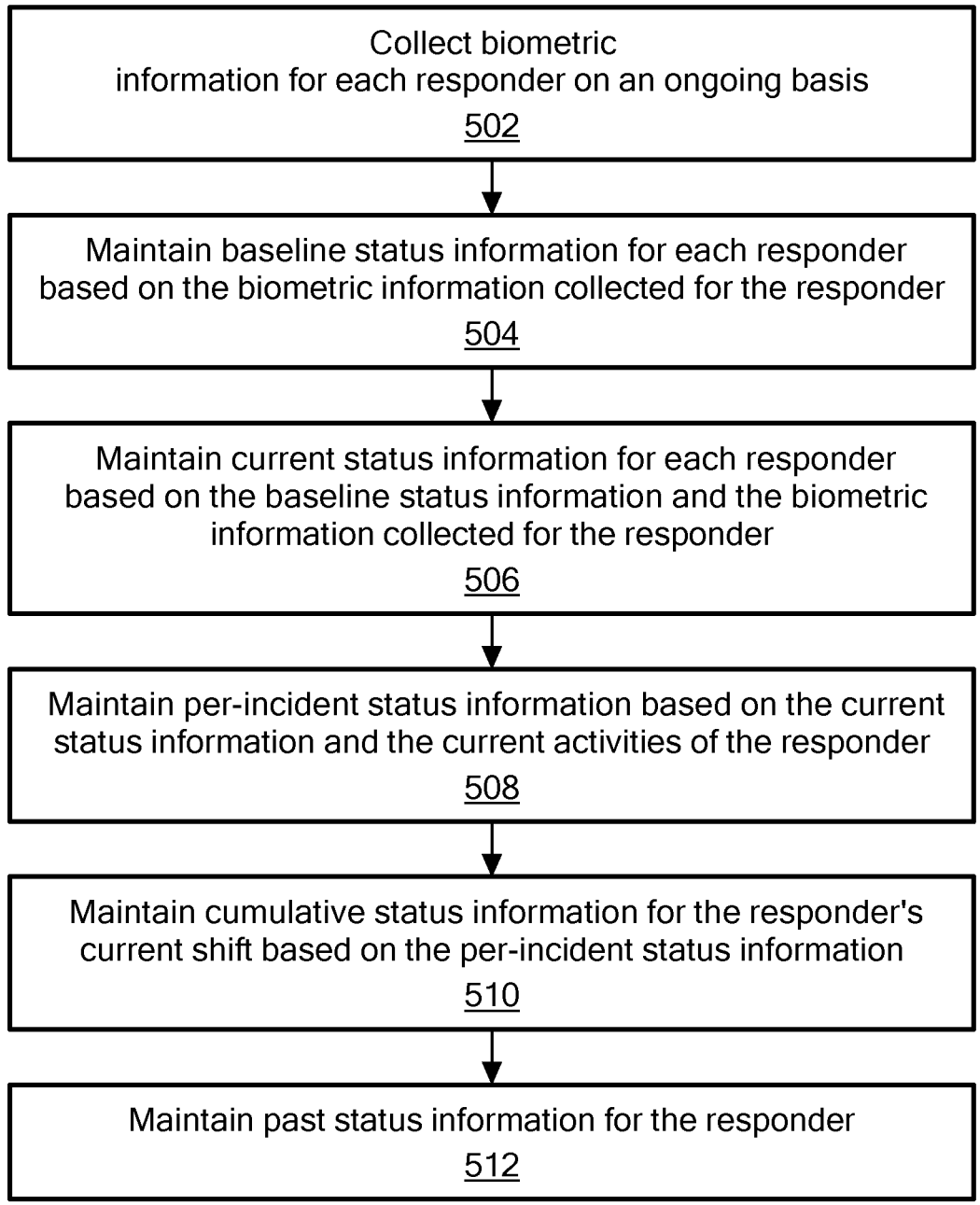
FIG. 5 is a schematic logic flow diagram for collection and processing of responder biometric information by the CAD server subsystem, in accordance with certain exemplary embodiments.

FIG. 5 is a schematic logic flow diagram for collection and processing of responder biometric information by the CAD server subsystem 110, in accordance with certain exemplary embodiments. In block 502, the CAD server subsystem 110 collects biometric information for each responder on an ongoing basis and stores this information in the database system 113. Specifically, in this exemplary embodiment, the mobile responder server 112 interfaces with the mobile responder client device 131 to collect biometric and other information from the wearable monitor device 132 and/or the mobile responder client device 131 and stores the collected information in the database system 113.

The collected information also may be fed to the machine learning service 114, which may be part of the CAD dispatch server 111 or may be separate from the CAD dispatch server 111, and which tracks the data over time. The machine learning service 114 typically is "self-calibrated" by historical data per responder over the entire history of monitoring of the responder. The machine learning service 114 also analyzes the collected information by incident type over time per responder. The machine learning service 114 can be queried (e.g., by the CAD dispatch server 111) for analytical data relating to such things as baseline status information for a given responder, current status information for a given responder, how a particular responder (or responders in general) have handled a given situation in the past, and how a particular responder (or responders in general) have responded or recovered after handling a given situation in the past, to name but a few.

The machine learning server 114 typically analyzes the collected information to learn about variances in the responder's biometric information based on a modified standard deviation analysis, e.g., to determine baseline biometric levels or to determine when the responder's biometric levels are abnormal (e.g., either too high or too low). In one specific exemplary embodiment, the standard deviation of an entire set of biometric information (or population) is known as σ (sigma) and is calculated using:

$$\sigma = \sqrt{\frac{\Sigma (x - \mu)^2}{N}}$$

where x represents each value in the population, μ is the mean value of the population, Σ is the summation (or total), and N is the number of values in the population.

Furthermore, in one specific exemplary embodiment, the standard deviation of a sample is known as S and is calculated using:

$$s = \sqrt{\frac{\sum(x-\bar{x})^2}{n-1}}$$

where x represents each value in the population, x is the mean value of the sample, Σ is the summation (or total), and n−1 is the number of values in the sample minus 1.

In block 504, the CAD server subsystem 110 maintains baseline status information for each responder based on the biometric information collected for the responder. For example, the CAD server subsystem 110 typically maintains a baseline value or baseline range for each of a number of biometric categories such as heart rate, skin temperature, and galvanic skin response for the responder. The baseline value or range essentially defines what is "normal" for the responder when the responder is not under duress (e.g., when the responder is at rest). In this exemplary embodiment, the baseline biometric information is stored as part of the Responder Record maintained for the responder. The CAD server subsystem 110 additionally may determine a baseline stress level for the responder and store the baseline stress level in the Responder Record maintained for the responder.

In block 506, the CAD server subsystem 110 determines current status information for each responder based on the baseline status information and the biometric information collected for the responder. In this specific exemplary embodiment, the CAD server subsystem 110 (e.g., the CAD dispatch server 111) compares recent biometric information collected for the responder against the baseline biometric information stored for the responder to determine whether or not the responder is under duress, and if so, the CAD server subsystem 110 may determine a relative stress level for the responder, e.g., whether the responder is mildly stress or extremely stressed assuming an elevated stress level is present. In this exemplary embodiment, the current biometric information and current stress level is stored in the Responder Record maintained for the responder along with other types of information such as, for example, the responder's current disposition (e.g., available or unavailable), current location, and other information (e.g., environmental information), to name but a few.

In block 508, the CAD server subsystem 110 determines per-incident status information based on the current status information relative to the current activities of the responder. For example, if the responder is currently responding to a particular type of incident, then the CAD server subsystem 110 can characterize how this particular responder reacted to this particular type of incident.

In block 510, the CAD server subsystem 110 maintains cumulative status information for the responder's current shift based on the per-incident status information. For example, the CAD server subsystem 110 may correlate the current status information with the per-incident status information associated with all incidents to which the responder was dispatched during the shift. Among other things, the cumulative status information can allow the CAD server subsystem 110 to identify potential issues with the remainder of the responder's shift, such as the responder being overly stressed or tired in view of the various incidents already handled by the responder during the shift.

In block 512, the CAD server subsystem 110 maintains past status information for the responder, which is essentially an archive of some or all of the other types of information collected and derived for the responder.

Figure 6:
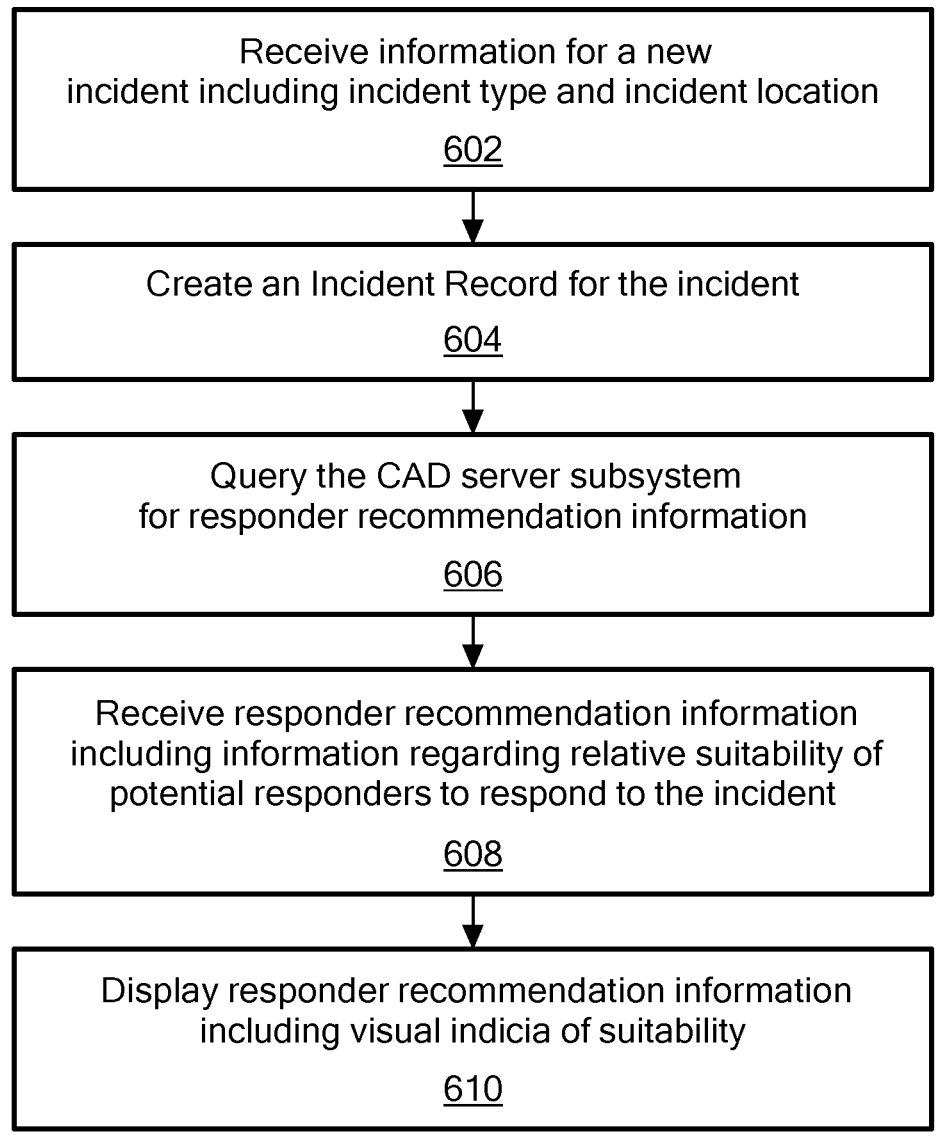
FIG. 6 is a schematic logic flow diagram for the dispatcher subsystem, in accordance with certain exemplary embodiments.

FIG. 6 is a schematic logic flow diagram for the dispatcher subsystem 120, in accordance with certain exemplary embodiments. In block 602, the dispatcher subsystem 120 receives information for a new incident including incident type and incident location, e.g., entered manually by a dispatcher and/or received electronically such as from an automated response system (e.g., 911 call center). In block 604, the dispatcher subsystem 120 creates an Incident Record for the incident. In block 606, the dispatcher subsystem 120 queries the CAD server subsystem 110 for responder recommendation information. In block 608, the dispatcher subsystem 120 receives responder recommendation information including information regarding relative suitability of potential responders to respond to the incident. In block 610, the dispatcher subsystem 120 displays responder recommendation information on the CAD dispatch client workstation 121 including visual indicia of suitability.

Figure 7:
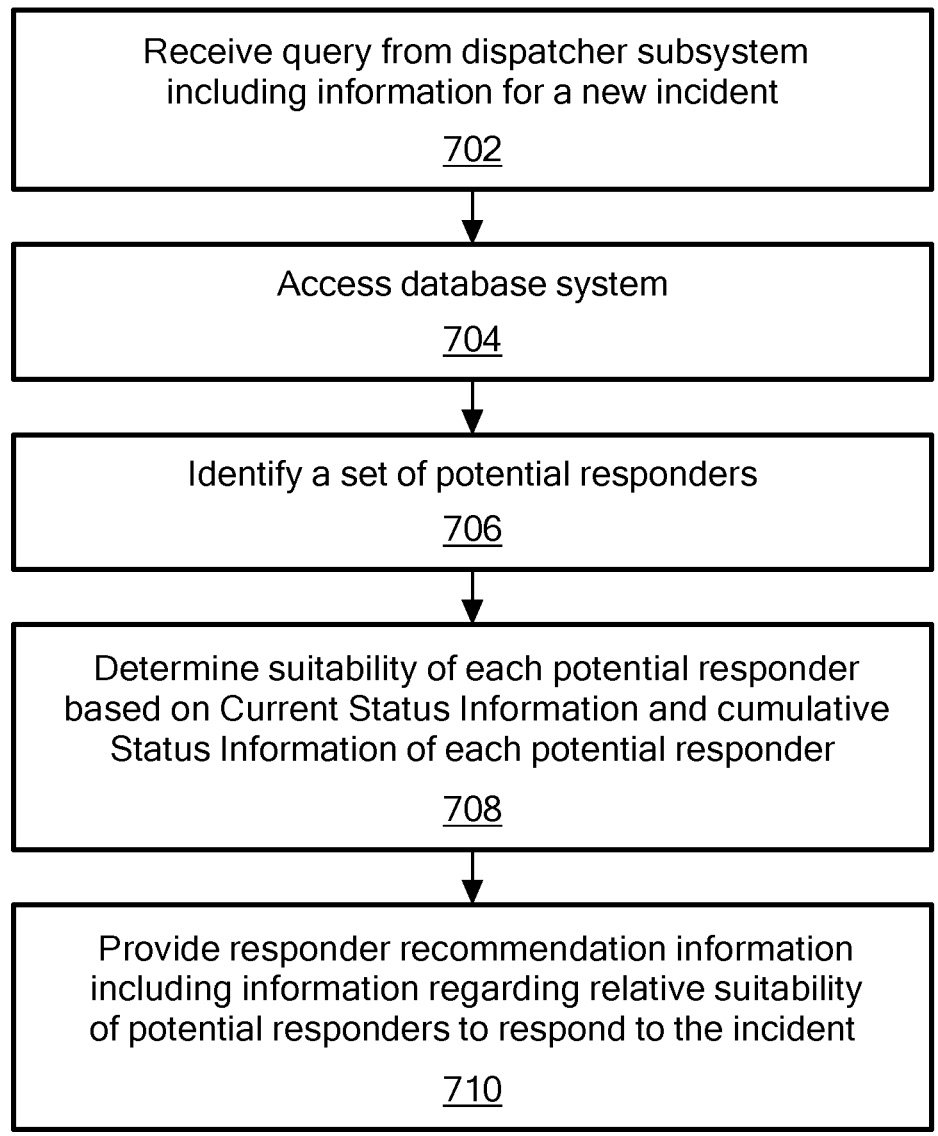
FIG. 7 is a schematic logic flow diagram for generating responder recommendation information for an incident by the CAD server subsystem, in accordance with certain exemplary embodiments.

FIG. 7 is a schematic logic flow diagram for generating responder recommendation information for an incident by the CAD server subsystem 110, in accordance with certain exemplary embodiments. In block 702, the CAD server subsystem 110 receives a query from a dispatcher subsystem 120 including information for a new incident. In block 704, the CAD server subsystem 110 accesses the database system 113. In block 706, the CAD server subsystem 110 identifies a set of potential responders. In block 708, the CAD server subsystem 110 determines suitability of each potential responder based on Current Status Information and cumulative Status Information of each potential responder. In block 710, the CAD server subsystem 110 provides responder recommendation information including information regarding relative suitability of potential responders to respond to the incident.

Figure 8:
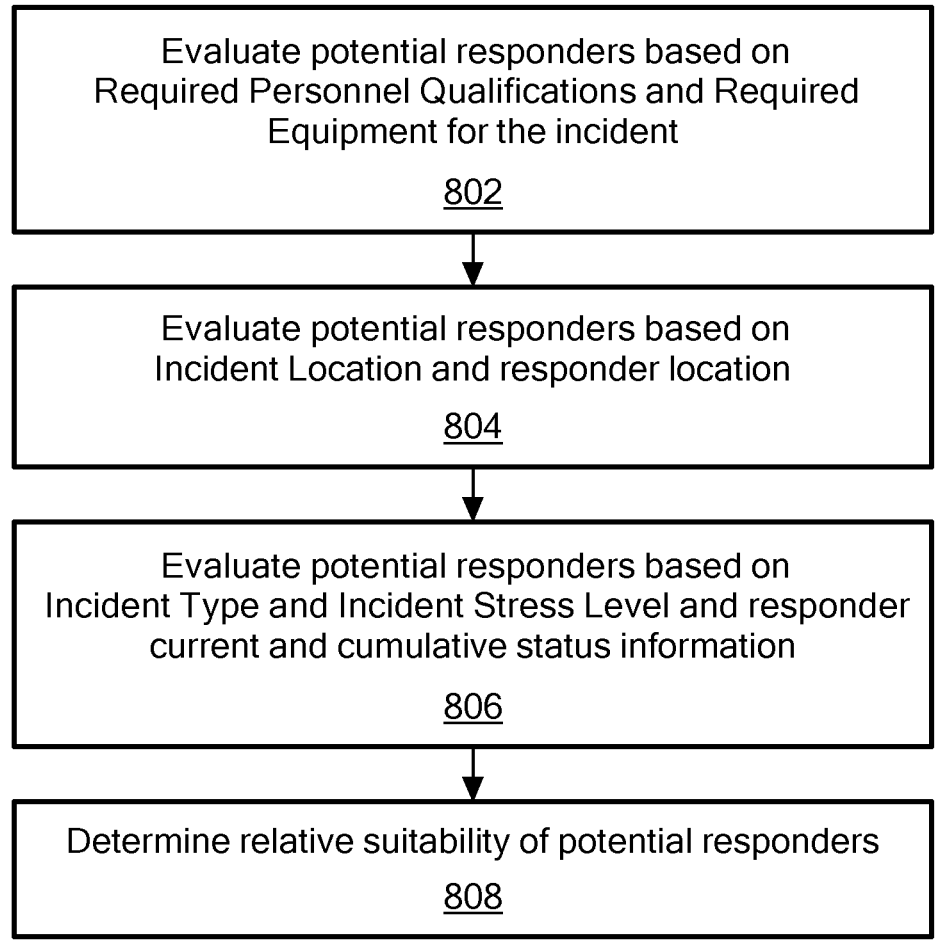
FIG. 8 is a schematic logic flow diagram for determining suitability of each potential responder based on Current Status Information and cumulative Status Information of each potential responder, in accordance with certain exemplary embodiments.

FIG. 8 is a schematic logic flow diagram for determining suitability of each potential responder based on Current Status Information and cumulative Status Information of each potential responder, in accordance with certain exemplary embodiments. In block 802, the CAD server subsystem 110 evaluates potential responders based on Required Personnel Qualifications and Required Equipment for the incident. In block 804, the CAD server subsystem 110 evaluates potential responders based on Incident Location and responder location (e.g., how long it would take the responder to reach the incident, which may include an analysis of current traffic conditions). In block 806, the CAD server subsystem 110 evaluates potential responders based on Incident Type and Incident Stress Level and responder current and cumulative status information. In block 808, the CAD server subsystem 110 determines relative suitability of potential responders based on the above evaluations, e.g., by using a weighting scheme to weigh the relative importance of responder qualifications, responder location (e.g., time for the responder to reach the incident), and current and cumulative biometric and stress levels with respect to the particular incident. For example, for some types of incidents, it might be more important to get a responder to the incident quickly even if the responder is less qualified and/or more stressed than other potential responders, while for some other types of incidents, it might be more important to send a responder who is more qualified and/or less stressed than other potential responders even if it will take a bit longer to get to the incident (e.g., a robbery with fleeing suspects might be better served by a 25 year old who runs marathons than a 55 year old who is in relatively poor physical condition).

By way of example, say that a particular responder has the following normalized status scores in three categories with respect to an emergency incident: Time to Arrival=8 (where 10=low time to arrival and 1=long time to arrival); Stress Level=5 (where 10=low stress and 1=high stress); and Qualification Match=3 (where 1=low qualification match and 10=high qualification match). In this example, normalized status scores can be computed from current status information of the potential responder and requirements for the particular incident type. It should be noted that embodiments are not required to use normalized status scores, but normalized status scores are used here for the sake of simplicity. Each of the three categories has a corresponding weight that is generally based on the type of incident. For example, some incidents might put a high weight on time to arrival, while other incidents might put a high weight on stress level or qualifications.

FIG. 13 provides one example of weighting for the three categories, in accordance with one exemplary embodiment. Here, for an incident type A, time to arrival has a weight of 80%, stress level has a weight of 10%, and qualification match has a weight of 10%. Based on the normalized status scores in the above example, this particular responder ends up with a final score of 7.2, which then can be evaluated against the scores of other potential responders in order to make recommendations to the dispatcher.

FIG. 14 provides another example of weighting for the three categories, in accordance with another exemplary embodiment. Here, for an incident type B, time to arrival has a weight of 40%, stress level has a weight of 40%, and qualification match has a weight of 20%. Based on the normalized status scores in the above example, this particular responder ends up with a final score of 5.8, which then can be evaluated against the scores of other potential responders in order to make recommendations to the dispatcher.

When evaluating responder stress levels, the CAD server subsystem 110 generally evaluates responder biometric information in view of the amount of time that has elapsed between various measurements. For example, if a particular responder has a baseline heart rate of 60 beats per minute and a current heart rate of 120 beats per minute after responding to a prior incident, the stress level determination for the responder generally would depend on how much time has elapsed since the prior incident, e.g., the responder may be considered highly stressed if an hour had elapsed since the prior incident and the heart rate is still high but may be considered only moderately stressed if only a few minutes had elapsed since the prior incident. In this regard, the CAD server subsystem 110 also may take into consideration past status information that contextualizes the current status information relative to the baseline information, such as how long it normally takes for the responder or an average responder to recover from a stressful situation. Thus, for example, if the responder's heart rate generally returns to normal in half an hour but the heart rate is still elevated after an hour, then that might be an indication that the responder is overly stressed.

Additionally or alternatively, the CAD server subsystem 110 may evaluate stress levels based on the amount of time it would take for the responder to reach the incident and a prediction of how that amount of time might affect the responder's stress level. For example, in some cases, a responder's stress level might increase while en route to an incident (e.g., in anticipation of a high-stress encounter), while in other cases, a responder's stress level might decrease while en route to an incident (e.g., where the time provides a "cooling off" period for the responder from a previous incident). Such evaluation of the potential effect of time on stress level can be based on current, cumulative, and/or past status information for the responder and across multiple responders (e.g., average amount of time it takes for a responder to recover from a stressful incident). Thus, such a CAD system can project future status of the responder and make recommendations accordingly.

Figure 9:
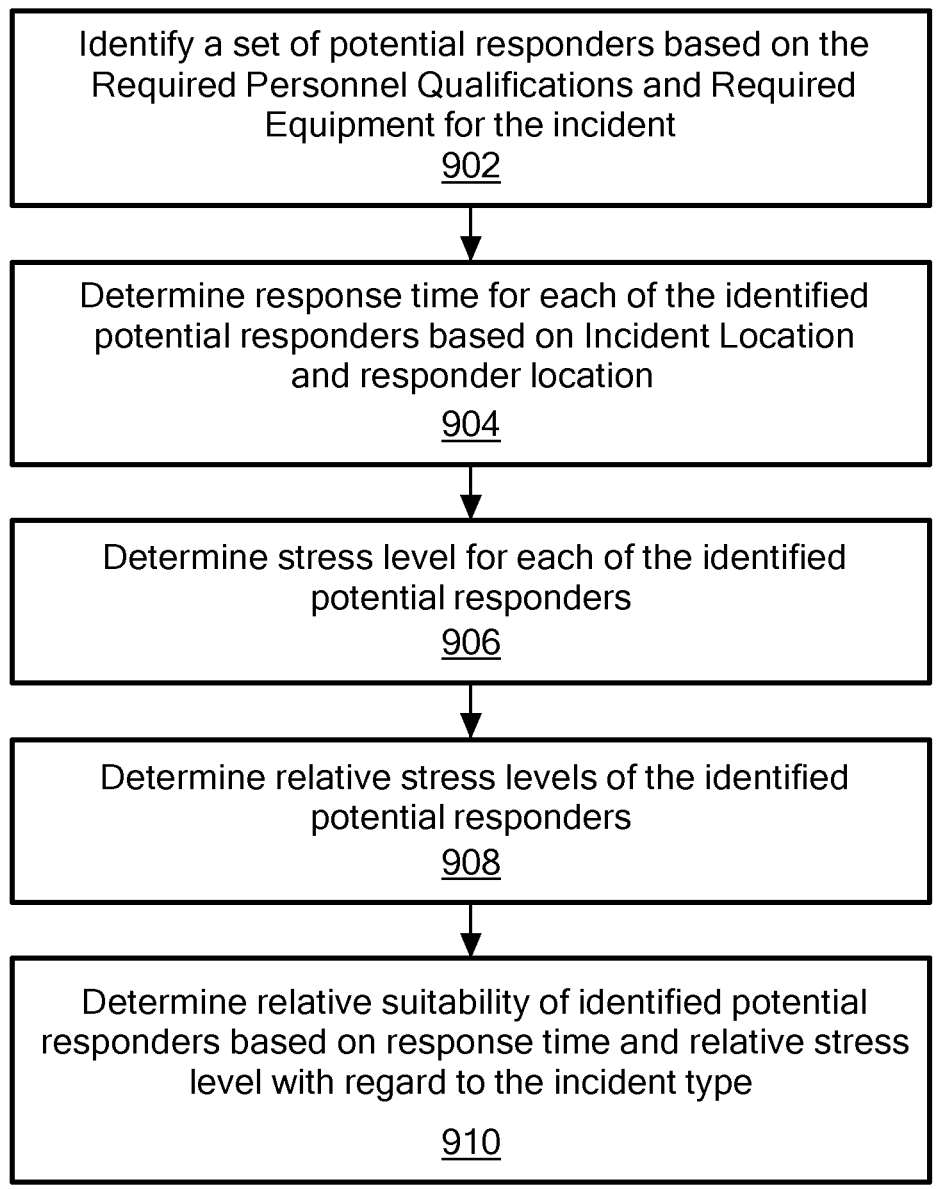
FIG. 9 is a schematic logic flow diagram for determining relative suitability of potential responders, in accordance with certain exemplary embodiments.

FIG. 9 is a schematic logic flow diagram for determining relative suitability of potential responders, in accordance with certain exemplary embodiments. In block 902, the CAD server subsystem 110 identifies a set of potential responders based on the Required Personnel Qualifications and Required Equipment for the incident. In block 904, the CAD server subsystem 110 determines response time for each of the identified potential responders based on Incident Location and responder location. In block 906, the CAD server subsystem 110 determines stress level for each of the identified potential responders. In block 908, the CAD server subsystem 110 determines relative stress levels of the identified potential responders. In block 910, the CAD server subsystem 110 determines relative suitability of identified potential responders based on response time and relative stress level with regard to the incident type.

Figure 15:
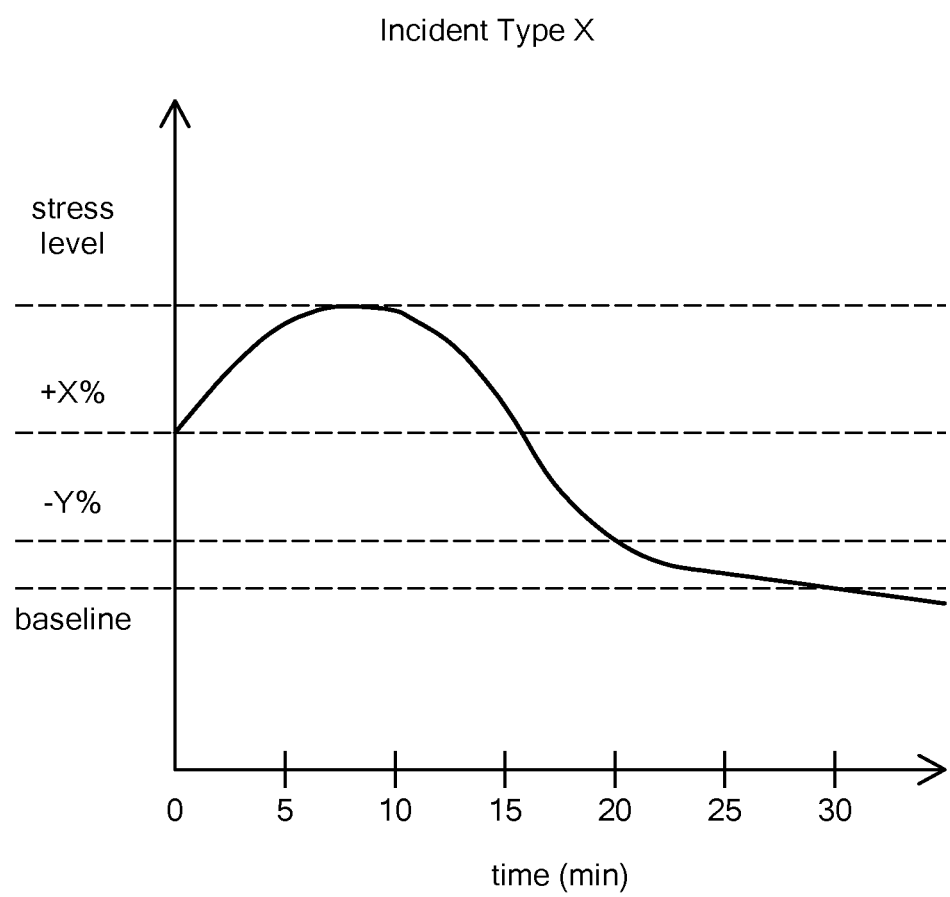
FIG. 15 is a schematic diagram of a graph showing an example recovery curve for a responder following a stressful incident, in accordance with one exemplary embodiment.

FIG. 15 is a schematic diagram of a graph showing an example recovery curve for a responder following a stressful incident. In this example, time 0 represents the end of a particular stressful incident, and this curve shows the stress level of the responder increasing for approximately 5-10 minutes and then decreasing in various stages for the next 20 minutes or so until the responder's stress level reaches the responder baseline stress level. The CAD system may generate a recovery curve for the responder based on the various types of status information collected for the responder. The CAD system may generate different recovery curves for different types of incidents that the responder has handled. The CAD system can use such curves to project a future stress level for the responder, for example, when evaluating responders for suitability for a particular emergency incident.

By way of example, assume the responder just ended a stressful incident and is being evaluated for suitability for another emergency incident. As described above, the CAD system can determine the current stress level of the responder, but the CAD system also may project the future stress level of the responder at the time the responder would arrive at the next emergency incident. For example, the CAD system may select or generate a recovery curve for the responder based on the just-completed emergency incident. For the sake of this example, it is assumed that the curve in FIG. 13 is the recovery curve for the just-completed emergency incident. If the next emergency incident is 10 minutes away, then the CAD system might project that the responder's stress level at the time of arrival will be increased (e.g., by X %) from the responder's current stress level based on the stress level change between time t(0) and time t(10) in the curve shown in FIG. 13. However, if the next emergency incident is 20 minutes away, then the CAD system might project that the responder's stress level at the time of arrival might be decreased (e.g., by Y %) from the responder's current stress level based on the stress level change between time t(0) and time t(20) in the curve shown in FIG. 13. Rather than using the responder's current stress level to evaluate suitability of the responder for the next emergency incident, the CAD system can use the responder's projected stress level to evaluate suitability of the responder for the next emergency incident.

Figure 10:
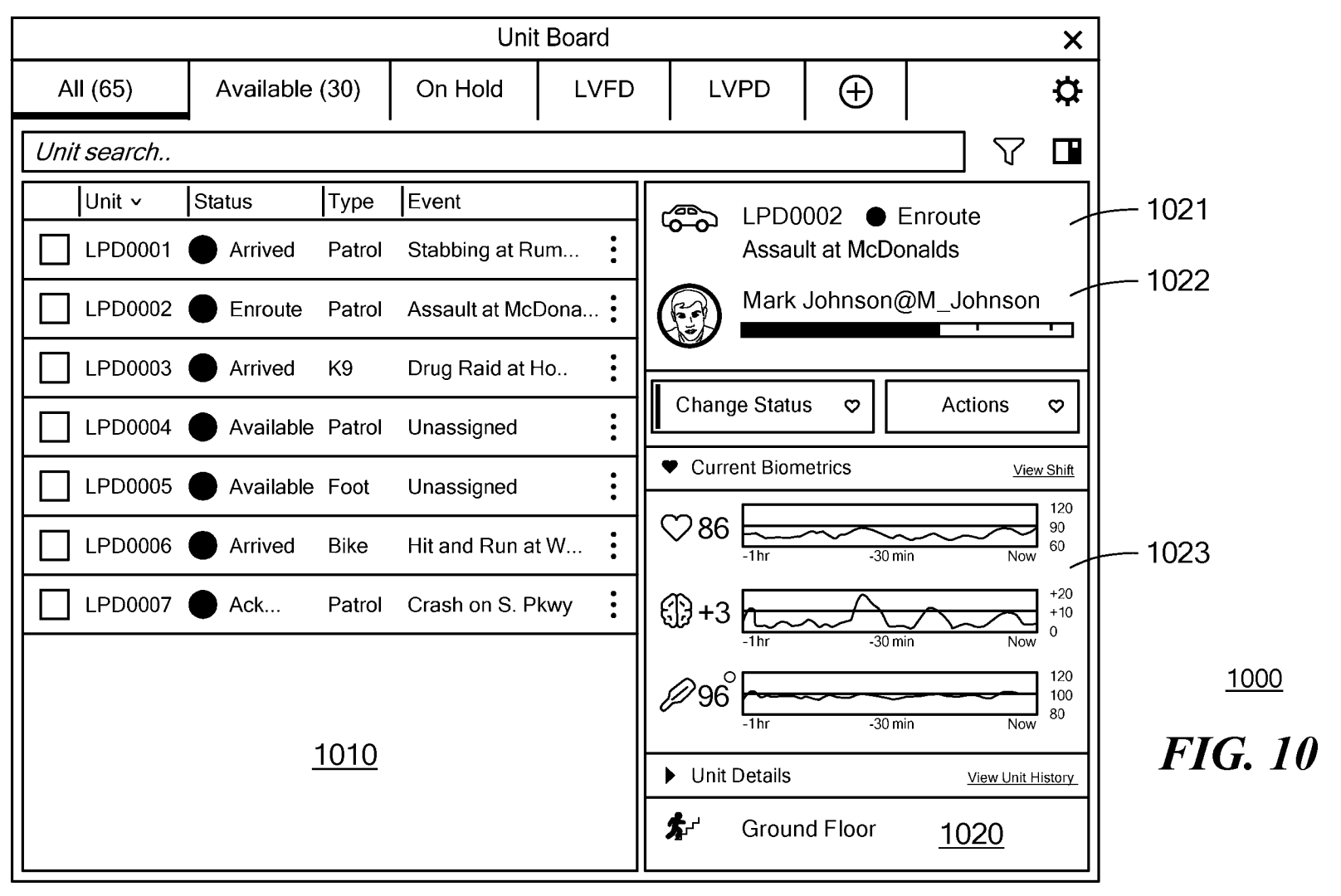

FIG. 10 is a schematic graphical user interface (GUI) screen 1000 of the type that may be displayed on the CAD dispatch client workstation 121, in accordance with certain exemplary embodiments. This GUI screen 1000 includes a first window area 1010 listing a number of units including, for each unit, a unit identifier (e.g., LPD0001-LPD0007), unit status information (e.g., arrived, enroute, available, etc.), unit type (e.g., patrol, K9, foot, bike, etc.), and an event (incident) description. In this example, the unit status information also includes color-coded indicia to assist the dispatcher with evaluating the status of each unit. In this example, the unit identified as LPD0002 is highlighted in the first window area 1010, which causes unit-specific status information to be displayed in a second window area 1020. In this example, the second window area 1020 shows unit information 1021 and status information for a specific responder associated with the unit (e.g., Mark Johnson) including stress level indicia 1022 and current biometrics 1023. In this example, the stress level indicia 1022 is in the form of a status bar with color-coded shading to show the responder's relative stress level, although it should be noted that the stress level indicia 1022 can be in other forms, such as, for example, a meter or a numerical value. The stress level indicia 1022 may include color-coding, such as green to indicate that the responder stress level is low, yellow to indicate that the responder stress level is medium, and red to indicate that the responder stress level is high. The current biometrics 1023 show specific biometric information in both numeric form (e.g., heart rate 86, brain activity +3, temperature 98) and graph form. The stress level indicia 1022 is derived at least in part from the current biometrics 1023.

Figure 11:
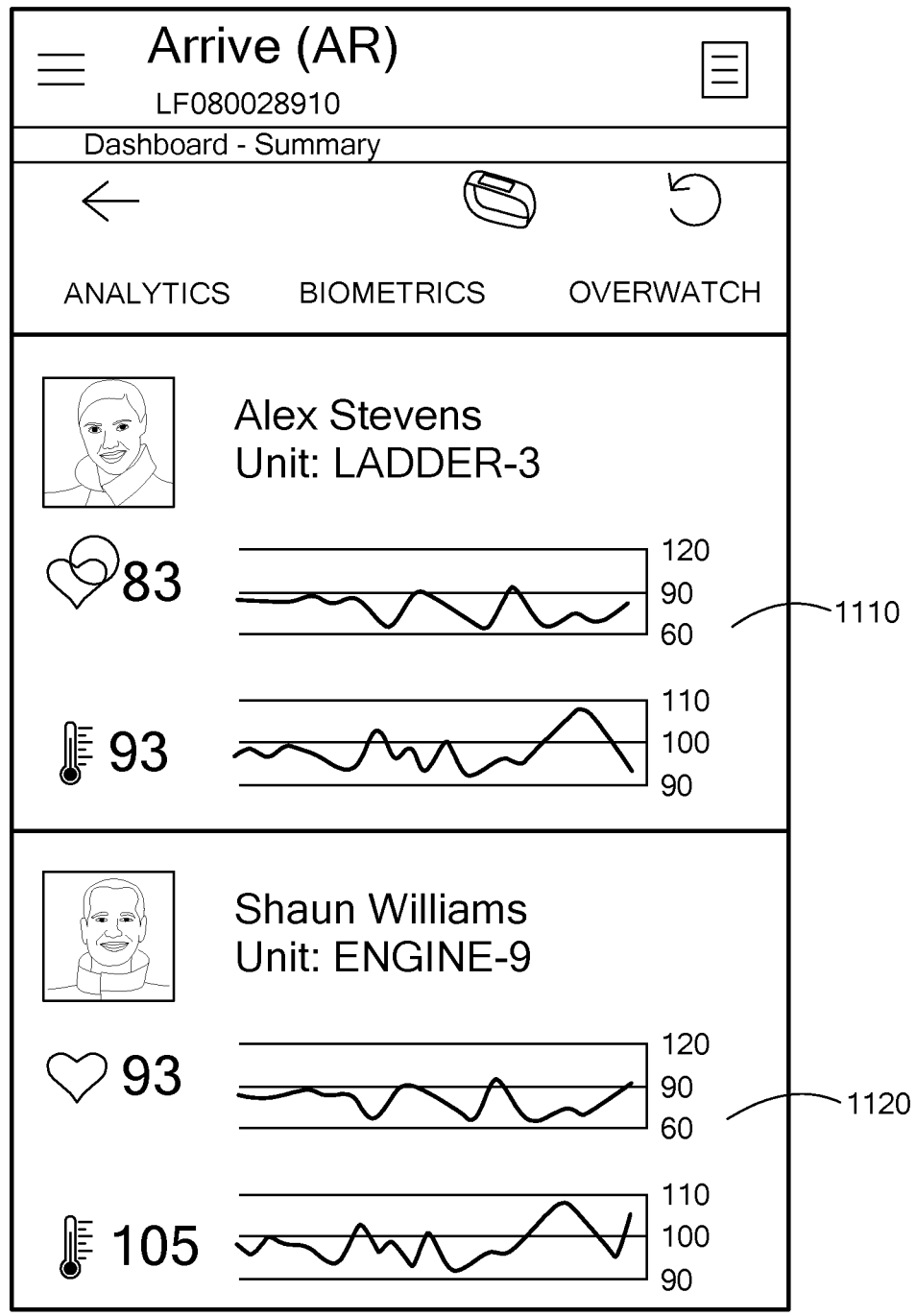
FIG. 11 is a schematic graphical user interface (GUI) screen of the type that may be displayed on the mobile responder client device, in accordance with certain exemplary embodiments.

In certain exemplary embodiments, the CAD server subsystem 110 can send similar types of information to the mobile responder client device 132 to be displayed to the user. FIG. 11 is a schematic graphical user interface (GUI) screen 1100 of the type that may be displayed on the mobile responder client device 132, in accordance with certain exemplary embodiments. In this example, the GUI screen 1100 displays status information for various responders (in this example, one responder named Alex Stevens in a window area 1110 and another responder named Shaun Williams in another window area 1120), which, in this example, includes heart rate and temperature information but in other embodiments may include additional and/or alternative information including stress level indicia of the type described above with reference to FIG. 10. The user may be able to scroll up and down to view status information for other responders.

FIG. 12 is a schematic graphical user interface (GUI) screen 1200 showing the types of information that may be provided to the dispatcher to assist with making a dispatch decision, in accordance with certain exemplary embodiments. In this example, the GUI screen 1200 includes an incident identifier, an incident description, an incident stress level indication (e.g., 6 out of 10, with 10 being the greatest stress level), and listing of available units ordered according to suitability. In this example, the CAD server subsystem 110 recommends that unit LPD0005 (a foot unit) respond to the incident, with unit LPD0004 (a patrol unit) as an alternative but ranked lower because the current officer stress level associated with unit LPD0004 is high (e.g., due to the unit having responded to a prior high-stress incident) and the incident is a high stress level incident. Ultimately, the dispatcher makes a dispatch decision, which could be to dispatch the unit recommended by the CAD server subsystem 110 or to dispatch a different unit.

In addition to use in making dispatch recommendations for specific incidents, exemplary embodiments of the CAD server subsystem 110 can monitor the status of each emergency responder on an ongoing basis based on the information collected from the personnel subsystems 130 and can make recommendations to the dispatcher for various types of actions.

For example, based on the information collected from the personnel subsystems 130, the CAD server subsystem 110 may identify when a particular responder is under duress and needs assistances from another emergency responder. This can occur, for example, when the emergency responder is en route to an incident, attending to an incident, or after completion of an incident. The emergency responder can be under duress for any of a variety of reasons, for example, due to increased stress levels, exhaustion, injury, or incapacitation (e.g., an "office down" situation).

In this regard, the CAD server subsystem 110 additionally may make recommendations to the dispatcher to change a dispatch decision. For example, if a particular emergency responder has been dispatched to an incident but the CAD server subsystem 110 identifies that the status of the emergency responder has changed since being dispatched and is now less suitable for the incident than another emergency responder, the CAD server subsystem 110 may provide notification to the dispatcher regarding the changed status of the emergency responder and/or the recommendation to dispatch a different emergency responder.

Thus, the CAD server subsystem 110 monitors the emergency responders and provides updates to the dispatcher dynamically and in real-time.

The CAD server subsystem 110 also can utilize a wide variety of analytics to provide information for non-dispatch decisions, such as monitoring status information for individual responders as well as aggregate status information across multiple responders to identify individual and group trends that then can be addressed such as with additional training, physical and mental therapy, or changes in policies, procedures, or equipment. For one example, if the CAD server subsystem 110 identifies that a particular responder tends to get overly stressed when responding to a particular type of incident or generally, then special training or therapy can be provided for that responder to deal with that type of incident.

It should be noted that it would be virtually impossible to describe herein all or even a large percentage of possible incident type and emergency responder scenarios to demonstrate how various embodiments of the present invention can utilize the various types of collected information to make dispatch and other recommendations. It will be clear to persons having ordinary skill in the art how the collected information can be used in various ways and scenarios to evaluate responder stress levels and overall/relative responder suitability that take into account responder stress levels and other parameters such as responder qualifications, cumulative status information for the responder's current or last shift, and time to respond to an incident.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an embodiment of the present invention, predominantly all of the reordering logic may be implemented as a set of computer program instructions that is converted into a computer executable form, stored as such in a computer readable medium, and executed by a microprocessor within the array under the control of an operating system.

Computer program logic implementing all or part of the functionality previously described herein may be embodied in various forms, including, but in no way limited to, a source code form, a computer executable form, and various intermediate forms (e.g., forms generated by an assembler, compiler, networker, or locator.) Source code may include a series of computer program instructions implemented in any of various programming languages (e.g., an object code, an assembly language, or a high-level language such as Fortran, C, C++, C#, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web.)

Hardware logic (including programmable logic for use with a programmable logic device) implementing all or part of the functionality previously described herein may be designed using traditional manual methods, or may be designed, captured, simulated, or documented electronically using various tools, such as a hardware description language (e.g., VHDL or AHDL), or a PLD programming language (e.g., PALASM, ABEL, or CUPL.)

While the invention has been particularly shown and described with reference to specific embodiments, it will be understood by those skilled in the art that various changes in form and detail may be made therein without departing from the spirit and scope of the invention as defined by the appended clauses. As will be apparent to those skilled in the art, techniques described above for panoramas may be applied to images that have been captured as non-panoramic images, and vice versa.

What is claimed is:

1. A computer-aided dispatch (CAD) system comprising:
a CAD database; and
a CAD server subsystem configured to:
store, in the CAD database, incident type information for each of a plurality of incident types, the incident type information specifying personnel qualifications for the incident type;
receive, for each of a plurality of responders, biometric sensor data generated by a biometric sensor device worn by the responder;
store, in the CAD database, the received biometric sensor data;
store, in the CAD database, past performance evaluation information for each of a plurality of responders, the past performance evaluation information characterizing how the responder has performed when responding to past instances of each of the plurality of incident types based on the biometric sensor data;
receive information for an incident including an incident type;
identify a set of available responders qualified to respond to the incident based on the stored personnel qualifications for the incident type;
evaluate relative suitability of the identified responders for the incident based on the past performance evaluation information characterizing how the identified responders have performed when responding to past instances of the incident type to determine a most suitable responder for handling the incident; and
produce a dispatch recommendation identifying the most suitable responder for handling the incident.

2. The system according to claim 1, wherein the past performance evaluation information characterizes how the responder reacts to each incident type.

3. The system according to claim 1, wherein the past performance evaluation information characterizes how the responder has recovered from past instances of the incident type.

4. The system according to claim 3, wherein the information characterizing how the responder has recovered from past instances of the incident type includes past biometric information and past stress level information from past instances of the incident type.

5. The system according to claim 1, wherein evaluating the relative suitability of the identified responders for the incident comprises:
determining a stress level for each identified responder;
accessing the CAD database to obtain a predetermined level of performance required for the incident; and
determining whether a given responder can meet the level of performance required for the incident based on the determined stress level for the given responder.

6. The system according to claim 1, wherein evaluating the relative suitability of the identified responders for the incident comprises:
determining, for each identified responder, a projected level of performance for the given responder at an estimated time of arrival at an incident location based on a recovery curve derived for the given responder from past performance of the given responder for instances of the incident type.

7. The system according to claim 1, wherein identifying the set of available responders qualified to respond to the incident comprises:
identifying the set of available responders qualified to respond to the incident based on personnel qualifications for the incident type and responder qualification information stored in the CAD database.

8. The system according to claim 1, wherein evaluating relative suitability of the identified responders for the incident is further based on a current condition of each available responder determined using biometric sensor data received from a biometric sensor device worn by the responder and healthy range data for the responder stored in the CAD database.

9. The system according to claim 1, wherein evaluating relative suitability of the identified responders for the incident is further based on an estimated time of arrival for each responder based on a current location of the responder and an incident location.

10. The system according to claim 1, wherein evaluating relative suitability of the identified responders for the incident is further based on elapsed times between discrete activities of each responder.

11. A computer-aided dispatch (CAD) method comprising:
   storing, in a CAD database, incident type information for each of a plurality of incident types, the incident type information specifying personnel qualifications for the incident type;
   receiving, for each of a plurality of responders, biometric sensor data generated by a biometric sensor device worn by the responder;
   storing, in the CAD database, the received biometric sensor data;
   storing, in the CAD database, past performance evaluation information for each of a plurality of responders, the past performance evaluation information characterizing how the responder has performed when responding to past instances of each of the plurality of incident types based on the biometric sensor data;
   receiving, by a CAD server subsystem, information for an incident including an incident type;
   identifying, by the CAD server subsystem, a set of available responders qualified to respond to the incident based on the stored personnel qualifications for the incident type;
   evaluating, by the CAD server subsystem, relative suitability of the identified responders for the incident based on the past performance evaluation information characterizing how the identified responders have performed when responding to past instances of the incident type to determine a most suitable responder for handling the incident; and
   producing, by the CAD server subsystem, a dispatch recommendation identifying the most suitable responder for handling the incident.

12. The method according to claim 11, wherein the past performance evaluation information characterizes how the responder reacts to each incident type.

13. The method according to claim 11, wherein the past performance evaluation information characterizes how the responder has recovered from past instances of the incident type.

14. The method according to claim 13, wherein the information characterizing how the responder has recovered from past instances of the incident type includes past biometric information and past stress level information from past instances of the incident type.

15. The method according to claim 11, wherein evaluating the relative suitability of the identified responders for the incident comprises:
   determining a stress level for each identified responder;
   accessing the CAD database to obtain a predetermined level of performance required for the incident; and
   determining whether a given responder can meet the level of performance required for the incident based on the determined stress level for the given responder.

16. The method according to claim 11, wherein evaluating the relative suitability of the identified responders for the incident comprises:
   determining, for each identified responder, a projected level of performance for the given responder at an estimated time of arrival at an incident location based on a recovery curve derived for the given responder from past performance of the given responder for instances of the incident type.

17. The method according to claim 11, wherein identifying the set of available responders qualified to respond to the incident comprises:
   identifying the set of available responders qualified to respond to the incident based on personnel qualifications for the incident type and responder qualification information stored in the CAD database.

18. The method according to claim 11, wherein evaluating relative suitability of the identified responders for the incident is further based on a current condition of each available responder determined using biometric sensor data received from a biometric sensor device worn by the responder and healthy range data for the responder stored in the CAD database.

19. The method according to claim 11, wherein evaluating relative suitability of the identified responders for the incident is further based on an estimated time of arrival for each responder based on a current location of the responder and an incident location.

20. The method according to claim 11, wherein evaluating relative suitability of the identified responders for the incident is further based on elapsed times between discrete activities of each responder.

* * * * *